US006635233B2

(12) United States Patent
Kato et al.

(10) Patent No.: US 6,635,233 B2
(45) Date of Patent: Oct. 21, 2003

(54) CFI-TYPE ZEOLITE, PROCESS FOR PREPARATION OF THE SAME, CATALYST PREPARED FROM THE SAME, AND PROCESS FOR CONVERSION OF ORGANIC COMPOUNDS

(75) Inventors: Hajime Kato, Nagoya (JP); Masahito Yoshikawa, Nagoya (JP); Kazuyoshi Iwayama, Nagoya (JP); Shinichi Sakaguchi, Nagoya (JP); Naoyuki Uchiyama, Nagoya (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/812,282

(22) Filed: Mar. 20, 2001

(65) Prior Publication Data

US 2001/0034467 A1 Oct. 25, 2001

(30) Foreign Application Priority Data

Mar. 21, 2000 (JP) ........................................ 2000-078438

(51) Int. Cl.$^7$ ............................ C01B 39/48; B01J 29/06
(52) U.S. Cl. ....................... 423/706; 423/707; 423/708; 423/713; 423/716; 502/60
(58) Field of Search ................................ 423/706, 707, 423/708, 713, 716; 502/60

(56) References Cited

U.S. PATENT DOCUMENTS

| | | | |
|---|---|---|---|
| 4,496,776 A | 1/1985 | Edwards et al. | 568/827 |
| 4,549,017 A | 10/1985 | McEntire et al. | 544/168 |
| 4,613,673 A | 9/1986 | McEntire et al. | 556/100 |
| 4,675,411 A | 6/1987 | Sommer et al. | 546/292 |
| 4,686,315 A | 8/1987 | Beach et al. | 585/513 |
| 5,271,922 A | 12/1993 | Nakagawa | |

FOREIGN PATENT DOCUMENTS

WO    WO-9908961 A  *  2/1999

OTHER PUBLICATIONS

Kubota et al., "Synthetic investigation of CIT–5 catalyst," *Microporous and Mesoporous Materials*, vol. 37, 2000, pp. 291–301.*

Yoshikawa et al., "Synthesis, Characterization, and Structure Solution of CIT–5, a New, High–Silica, Extra–Large–Pore Molecular Sieve," J. Phys. Chem. B, vol. 102, 1998, pp. 7139–7147.*

Sita L., Xi, R., Yap, G., Liable–Sands, L., and Rheingold, A., "High Yield Synthesis and Characterization of $Sn_6(\mu_3-O)_4(\mu_3-OSi(CH_3)_3)_4$," 1997, J. Am. Chem. Soc., 119, 756–760.

K. Tsuji et al, "High–silica molecular sieve syntheses using the sparteine related compounds as structure–directing agents," *Microporous and Mesposorous Materials, Elsevier Science Publishing, New York*, vol. 28, No. 3,, May 1999, pp. 461–469, XP004165647, ISSN: 1387–1811.

Martinez–Triguero J. et al., "The Catalytic Performance of 14–Membered Ring Zeolites", *Journal of Catalysis, Academic Press, Dulutj, MN, US*, vol. 182, 1999, pp. 463–469, XP001000129, ISSN: 0021–9517.

* cited by examiner

*Primary Examiner*—David Sample
(74) *Attorney, Agent, or Firm*—Piper Rudnick LLP

(57) ABSTRACT

A CFI-type zeolite where the atomic ratio of silicon to the heteroatom is 45 or less and the long axes of the crystals are 0.7 μm or less is useful as a catalyst for conversion reaction of aromatic compounds because the zeolite has a number of active sites and small crystals.

9 Claims, 10 Drawing Sheets

CFI-TYPE ZEOLITE, PROCESS FOR PREPARATION OF THE SAME, CATALYST PREPARED FROM THE SAME, AND PROCESS FOR CONVERSION OF ORGANIC COMPOUNDS

BACKGROUND OF THE INVENTION

1. Field of the Invention

The present invention relates to a CFI-type zeolite containing fourteen-membered ring pores useful as a conversion catalyst for organic compounds, a process for the preparation of the zeolite, a catalyst prepared from the zeolite, and a process for the conversion of organic compounds.

2. Description of Related Arts

The CFI-type zeolite is a zeolite containing novel fourteen-membered ring pores invented by Yoshikawa and Devis and also is called CIT-5. Processes for the synthesis and the structure of the zeolite are already disclosed by the following literatures:

Literature 1: WO99/08961

Literature 2: *Chemical Communications*, 2179 (1997)

Literature 3: *Journal of Physical Chemistry, B*, 102, 7139 (1998)

Literature 4: *Journal of Catalysis*, 182, 463 (1999)

Literature 5: *Shokubai*, 41, 380 (1999)

Literature 2 describes CIT-5 having a $SiO_2/Al_2O_3$ ratio of 50, but no physical shape thereof. Furthermore, the CIT-5 having a $SiO_2/Al_2O_3$ ratio of 50 could not be prepared according to the process as described therein. As described in Example 5 of literature 1, hydrothermal treatment of the reaction mixture having a known composition ($LiOH/SiO_2=0.1$ and methylsparteinium hydroxide/$SiO_2=0.2$) only produces a mixture containing amorphous materials without forming a finely crystallized CFI-type zeolite from the reaction mixture having a $SiO_2/Al_2O_3$ ratio of 100. The other literatures describe no CIT-5 having a $SiO_2/Al_2O_3$ ratio lower than 100, and also no CIT-5 having an atomic ratio of silicon to a heteroatom that is 45 or less. In literature 1, the synthesis of CIT-5 is carried out by use of the reaction mixture having a Si/Zn ratio of 25, but it is not clear whether zinc is contained in the resulting zeolite.

The CFI-type zeolite (CIT-5) contains a fourteen-membered ring pore which is large of the pore sizes of zeolites, and is expected as a novel material for catalysts. However, the related art has been unable to introduce a number of heteroatoms into the framework of the zeolite, that is, producing only CIT-5 having a small number of catalytic active sites. CIT-5 has a monodimensional pore of fourteen-membered ring size. The monodimensional pore is inferior in diffusion to multi-dimensional pores, and therefore smaller crystals are useful as catalysts. However, the related art has been unable to prepare CIT-5 having a number of active sites and furthermore small crystal size.

SUMMARY OF THE INVENTION

The invention aims at providing CIT-5 having a number of active sites and small crystal size, and more concretely a CFI-type zeolite where the atomic ratio of silicon to the heteroatom is 45 or less, and the long axes of the crystals are 0.7 μm or less.

The first invention of the invention is the CFI-type zeolite characterized in that the atomic ratio of silicon to the heteroatom is 45 or less, and the long axes of the crystals are 0.7 μm or less.

The second invention is a process for preparing the CFI-type zeolite characterized in that a reaction mixture satisfying the following both conditions (1) and (2) is subjected to hydrothermal treatment:

(1) $LiOH/SiO_2<0.15$ (in molar ratio)

(2) $ROH/SiO_2>0.2$ (in molar ratio, ROH represents an alkylsparteinium hydroxide).

The third invention is a catalyst containing the aforesaid CFI-type zeolite.

The fourth invention is a process for the conversion of organic compounds characterized by allowing the aforesaid catalyst to contact with the organic compounds.

DESCRIPTION OF THE PREFERRED EMBODIMENTS

Figure 1:
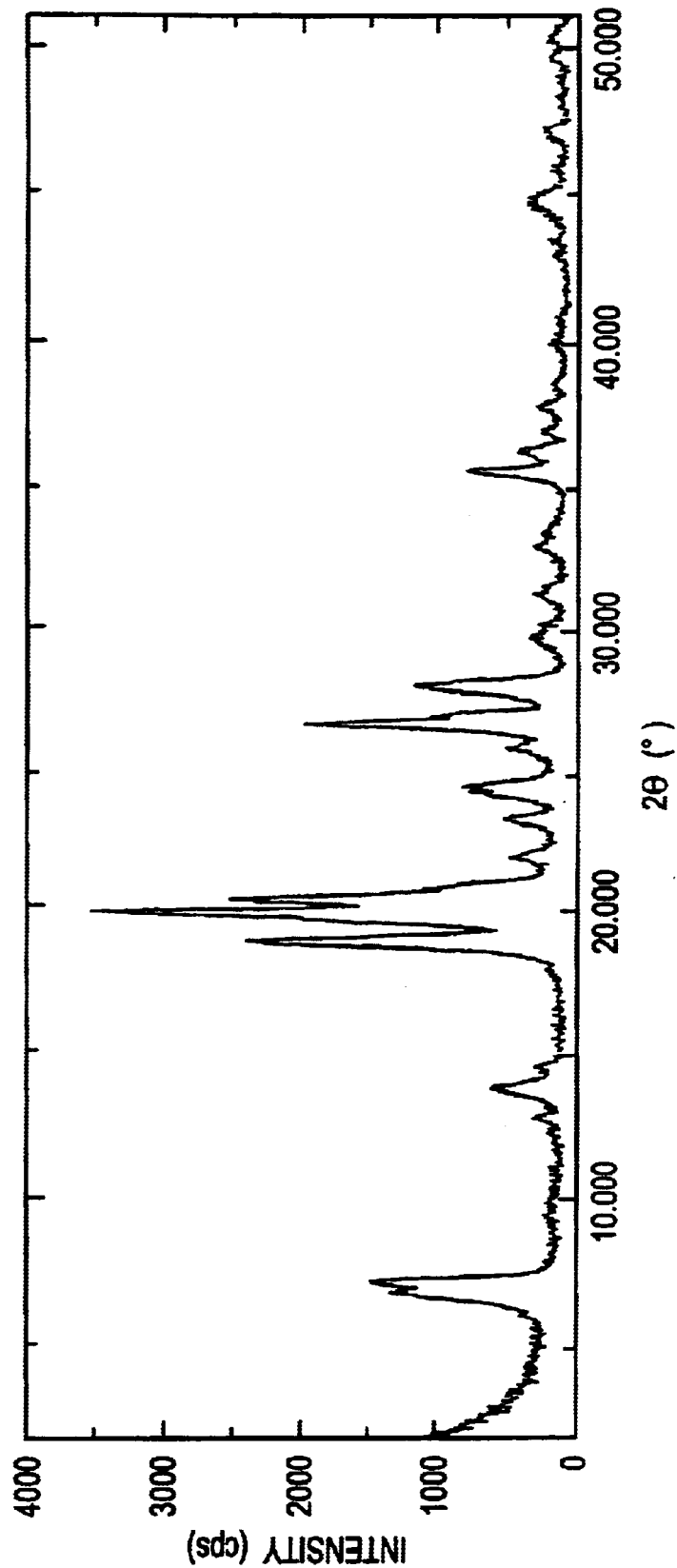
FIG. 1 is an X-ray diffraction pattern of CIT-5 synthesized in Example 1.

The first invention of this invention is "the CFI-type zeolite characterized in that the atomic ratio of silicon to the heteroatom is 45 or less, and the long axes of the crystals are 0.7 μm or less."

In the invention, the CFI-type zeolite means a zeolite having a framework structure similar to that of the CIT-5 zeolite first synthesized by Yoshikawa and Davis and having framework structure determined by Wagner. The Structure Commission of the International Zeolite Association gives codes consisting of three alphabetical letters to zeolites having structure determined, and zeolites having the same topology are generically called by such three letters. The code CFI is given to the structure of CIT-5, and therefore it is general that zeolites having a framework structure similar to that of CIT-5 are named a CFI-type zeolite.

The simplest method of examining whether a zeolite has the CFI-type framework structure is powder X-ray diffraction. In the powder X-ray diffraction pattern, the structure can be judged from the presence of peaks shown in Tables 1 and 2. Table 1 shows peak positions usually observed in the powder X-ray diffraction patterns of non-calcined CFI-type zeolites. Table 2 shows peak positions generally observed in the powder X-ray diffraction patterns of CFI-type zeolites after removing organic materials in pores by calcination.

TABLE 1

X-Ray Diffraction Peaks of Non-calcined CIT-5
Interplanar Spacing d (nm)

| |
|---|
| 1.27 ± 0.01 |
| 1.21 ± 0.01 |
| 0.690 ± 0.005 |
| 0.636 ± 0.005 |
| 0.468 ± 0.005 |
| 0.453 ± 0.005 |
| 0.444 ± 0.005 |
| 0.433 ± 0.005 |
| 0.424 ± 0.005 |
| 0.405 ± 0.005 |
| 0.380 ± 0.005 |
| 0.367 ± 0.005 |
| 0.361 ± 0.005 |
| 0.345 ± 0.005 |
| 0.333 ± 0.005 |
| 0.329 ± 0.005 |
| 0.316 ± 0.005 |
| 0.352 ± 0.005 |

TABLE 2

Typical X-Ray Diffraction Peaks of Calcined CIT-5
Interplanar Spacing d (nm)

| |
|---|
| 1.27 ± 0.02 |
| 1.21 ± 0.02 |
| 0.467 ± 0.005 |
| 0.444 ± 0.005 |
| 0.433 ± 0.005 |
| 0.425 ± 0.005 |
| 0.362 ± 0.005 |
| 0.332 ± 0.005 |

The zeolite herein means silicate-series crystalline microporous materials, which include crystalline alumino-silicates, crystalline metallo-silicates, and crystalline metallo-aluminosilicates having the CIT-5 (CFI) structure. Metallo-silicates and metallo-aluminosilicates mean herein aluminosilicates, part or all of aluminum therein are replaced with other metals than aluminum, other metals which include gallium, iron, titanium, boron, cobalt, and chromium. Elements forming the framework structure other than silicon and oxygen, for example, aluminum, gallium, iron, titanium, boron, cobalt, and chromium are herein defined as heteroatoms.

In the invention it is essential that the atomic ratio of silicon to the heteroatom is 45 or less. In the use of the zeolite as a catalyst, a low atomic ratio of silicon to the heteroatom is preferred, and therefore the ratio of 40 or less is more preferred. The lower limit of the atomic ratio is 1 based on the nature of the zeolite (Loewenstein's rule). In the use of the zeolite as a catalyst, the ratio in general is preferably 5 or more and most preferably 7 or more in view of acid strength, amount of acid site, and thermal stability. The atomic ratio of silicon to the heteroatom can be determined by the atomic absorption analysis, X-ray fluorescence spectrometry, and inductively coupled high-frequency plasma emission spectrometry (ICP method) and the like. Herein, the atomic ratio is not that of the reaction mixture used for synthesis, but that of a CFI-type zeolite formed practically.

Although the kinds of the heteroatoms are not particularly limited, preferred examples thereof include aluminum, gallium, iron, titanium, boron, cobalt, and chromium, more preferably aluminum, gallium, and boron, and most preferably aluminum because it has the strongest acid strength as catalyst.

Furthermore, in the CFI-type zeolite of the invention, it is essential that the long axes of the crystals are 0.7 $\mu$m or less. As it is expected that the zeolite of the invention is used as a catalyst, smaller crystals thereof are preferred because high diffusion of compounds within a pore brings about high activity to the catalyst. The size of the crystals can be measured by a scanning electron microscope. When a CFI-type zeolite is subjected to random sampling and observed by a scanning electron microscope, it is preferable that the long axes of crystals of at least 50 percent or more are 0.7 $\mu$m or less. In order to measure precisely the crystal size, observation at a magnification of ×40,000 is preferred. In the invention, the long axis means the longest length in a crystal. The shapes of the crystals are not particularly limited. Although tabular and needlelike crystals of CIT-5 in general are known, the shapes of the crystals are not limited to these.

When the heteroatom is a trivalent or divalent atom, the framework has a negative charge and needs a cation to compensate the charge. The kind of the cation is not particularly limited in the invention. All of a proton, alkali metals such as Li, Na, K, Rb, and Cs, alkaline earth metals such as Mg, Ca, Sr, and Ba, transition metals, noble metals, and rare earth elements can be used as the cation. These cations are not the heteroatoms of the invention.

The second invention of the invention is "the process for preparing the CFI-type zeolite characterized in that the reaction mixture having the following both conditions (1) and (2) is subjected to the hydrothermal treatment:

(1) LiOH/SiO$_2$<0.15 (molar ratio)

(2) ROH/SiO$_2$>0.2 (molar ratio, ROH represents an alkyl-sparteinium hydroxide)."

According to known processes for preparing CFI-type zeolites in related art, it has been impossible to decrease the atomic ratio of silicon to the heteroatom to less than 50. According to the process of the invention, however, the CFI-type zeolite synthesized has excellent efficiency as a catalyst wherein the atomic ratio of silicon to the heteroatom is less than 45, and the long axes of the crystals are 0.7 $\mu$m or less.

In the process for preparing the zeolite of the invention, the composition of the reaction mixture must satisfy both conditions of (1) LiOH/SiO$_2$<0.15 (in molar ratio) and (2) ROH/SiO$_2$>0.2 (in molar ratio. ROH is an alkylsparteinium hydroxide. The same shall apply hereinafter). LiOH exceeding this range is liable to form impurities such as cristobalite. A preferred range is 0.02<LiOH/SiO$_2$≦0.12.

ROH less than this range prevents crystallization from proceeding. As the amount of the heteroatom introduced increases, a larger ratio of ROH/SiO$_2$ is preferable. The value is preferably 0.25 or more, more preferably 0.30 or more, and most preferably 0.35 or more. The value ranges particularly preferably from 0.35 to 10.

ROH can contain therein an alkylsparteinium chloride or an alkylsparteinium iodide.

The alkyl groups of the alkylsparteinium hydroxide, the alkylsparteinium chloride, and the alkylsparteinium iodide are not particularly limited. Examples of the alkyl groups include a methyl, an ethyl, and a propyl, and the methyl is most preferred.

Methylsparteinium hydroxide that is most preferred of the alkylsparteinium hydroxides is the following compound:

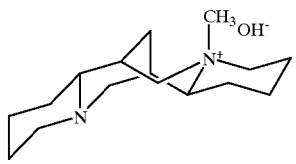

Although LiOH used for the preparation of the CFI-type zeolite is not particularly limited, anhydrous lithium hydroxide is preferred.

A process for synthesizing ROH used for the preparation of the CFI-type zeolite is not particularly limited. For example, spartein is alkylated with an alkyl halide, and then hydroxylated by use of an anion-exchange resin. An example is shown in Reference Example 1 as described later.

The sources of silica used for the preparation of the CFI-type zeolite are not particularly limited. Examples of the sources include colloidal silica, fumed silica, water glass, precipitated silica, and silicon alkoxides.

The sources of the heteroatoms used for the preparation of the CFI-type zeolite are not particularly limited. The usable sources of aluminum, gallium, iron, cobalt, and chromium include nitrates, sulfates, acetates, chlorides, hydroxides, oxides, and alkoxides, respectively. The usable sources of titanium are the nitrate, sulfate, chloride, oxide, and alkoxides thereof. The usable sources of boron are sodium borate, boric acid, the oxides, and the alkoxides. For example, when the heteroatom is aluminum, the usable sources thereof include aluminum salts such as aluminum nitrate, aluminum sulfate, and aluminum chloride, aluminum hydroxide, aluminum oxide, aluminum alkoxides. Preferably the usable source of aluminium is aluminium hydroxide in order to decrease the Si/Al ratio.

Aluminosilicates, metallo-silicates, and metallo-aluminosilicates can be used as the sources of heteroatoms and silica. The aluminosilicates, metallo-silicates, and metallo-aluminosilicates may be either crystalline or amorphous, and zeolites also can be used. Particularly, of the aluminosilicates, Y-type zeolite is most preferably used. The reason for this is that the Y-type zeolite has a high surface area, and can lead to the zeolite having various Si/Al ratios. It is preferred that the Y-type zeolite is changed into H-type or Li-type before using.

A source of silica, a source of the heteroatom, LiOH, ROH, and water are mixed according to the composition of the invention to prepare a reaction mixture for synthesize the zeolite. The order of adding these materials is not particularly limited. The mixture is desirably stirred. The reaction mixture is placed in a pressure vessel and heated. Although the heating temperatures are not limited as long as crystals are formed, 140° C. or above is preferred, and 160° C. or above is more preferred in order to obtain a sufficient crystallization rate. Heating with stirring is preferred.

The third invention of the invention is "the catalyst containing the CFI-type zeolite characterized in that the atomic ratio of silicon to the heteroatom is 45 or less and the long axes of the crystals are 0.7 µm or less, or the zeolite prepared by the aforesaid process."

The CFI-type zeolite characterized in that the atomic ratio of silicon to the heteroatom is 45 or less and the long axes of the crystals are 0.7 µm or less and the process for the preparation of the zeolite of the invention are as described above. Known processes can be utilized for the preparation of the catalyst from the zeolite of the invention. The most general process is herein illustrated. For the catalyst the zeolite formed in general is used. The formed product can be the zeolite singly formed or the zeolite granulated together with a binder such as alumina and clay. For the granulation, for example, the zeolite is kneaded together with a binder such as alumina sol, extruded with an extruder, and rounded with a marumerizer.

From the catalyst containing the CFI-type zeolite, crystal water in the zeolite and organic substances used in the synthesis are usually removed before using the catalyst. Almost all the crystal water and organic substances used in the synthesis can be usually removed by heating at 200 to 650° C.

The capability of the catalyst in general is improved by ion exchange after removing organic substances in the pores of the zeolite. For example, when it is used as an acid catalyst, the catalyst undergoes ammonium exchange in an aqueous solution of ammonium nitrate or ammonium chloride, and then calcined, thus to turn to an acid type. Furthermore, the catalyst also can be turned to an acid type by treatment with an acid such as hydrochloric acid or nitric acid.

In addition, in order to impart capabilities other than that as the acid catalyst, alkali metals, alkaline earth metals, transition metals, noble metals, rare earth elements also can be introduced into ion exchange sites. After introducing these metals into the ion exchange sites, the metals may exist in sites different from the ion exchange sites by the calcination of the zeolite.

The catalyst can contain metals, for example, in portions occupied by the binder other than those occupied by the zeolite. For example, when used as an acid catalyst, it is preferred that a noble metal is supported and reaction is carried out in the coexistence of hydrogen in order to lengthen the life of the catalyst. Although the reason for this is not clear, protons may be fed into the catalyst with ease, and coking be inhibited. Nobel metals supported are not particularly limited, but rhenium is most preferred probably because of low activity to hydrogenolysis.

When the CFI-type zeolite is used as a catalyst, the ratio of silicon to the heteroatom cannot be determined by elementary analysis in the case where some binders are used, but the ratio of silicon to the heteroatom can be determined by $^{29}$Si-NMR.

This catalyst is useful to conversion reaction and preferably isomerization reaction of aromatic compounds having three or more substituent groups on an aromatic ring. Preferred examples of the aromatics include dihalogenated toluenes, trihalogenated benzenes, and trialkylbenzenes. The zeolite contained in the catalyst is preferably of an acid type and further preferably contains rhenium.

The fourth invention of the invention is "the process for the conversion of the organic compounds characterized by allowing the aforesaid catalyst to contact with the organic compounds."

A method for allowing the catalyst to contact with the organic compounds is illustrated in detail below. In the invention, the organic compounds are not particularly limited, but preferably used for the conversion of compounds containing carbon. The organic compounds used preferably for the conversion are formed of carbon, oxygen, hydrogen, nitrogen, sulfur, chlorine, bromine, fluorine, phosphorus, and the like.

The kinds of the conversion reactions are not particularly limited. Examples of the conversion reactions include cracking, dewaxing, aromatization, decomposition, dimerization, polymerization, condensation, isomerization, disproportionation, oxidation, rearrangement, hydrogenation, esterification, and hydrolysis. Specifically, they include the cracking of heavy oil, the dewaxing of lubricants, the aromatization of paraffin, the deethylation of ethylbenzene, the dimerization of benzene, the polymerization to polyesters, the condensation of alcohols, the isomerization of substituted aromatics, the disproportionation of toluene, the hydroxylation of aromatics, Beckmann rearrangement, the hydrogenation of olefin, the esterification from acids and alcohols, and the hydrolysis of esters.

The CFI-type zeolite has a pore size of a fourteen-membered ring, 0.73 nm (7.3 angstroms), which is relatively large of the pore sizes of zeolites. Therefore, the zeolite is more preferably used in reactions where the reaction mixture of reaction is a large compound or the product is a large compound. For example, in substituted aromatics, large molecules include aromatic compounds substituted by a large group having two or more carbon atoms, aromatic compounds substituted by a halogen, and aromatic compounds having three or more substituent groups. The catalyst of the invention is effective to the conversion reactions of such compounds. The aromatic compounds having three or more substituent groups are those having three or more substituent groups on a benzene ring. The kinds of the substituent groups are not particularly limited, and examples thereof include halogens, hydrocarbons, a hydroxyl group, oxygen-containing hydrocarbons, halogen-containing hydrocarbons, and nitrogen-containing substituent groups. Examples of such aromatic compounds include trimethylbenzene, tetramethylbenzene, chloroxylene, dicholoroxylene, dichlorotoluene, trichlorobenzene, dichloroaniline, xylenol, trimethylphenol, and dimethylbenzoic acid. As a matter of course, the aromatic compounds are not limited to these examples. The catalyst in particular is effective to the compounds containing a halogen as at least one of the substituent groups. As the number of halogens substituted increases, the invention is more effective. Examples of the aromatic compounds having a halogen or a group having two or more carbon atoms as at least one of the substituent groups include chlorotoluene, bromotoluene, ethyltoluene, propyltoluene, diethyltoluene, butyltoluene, chloroethylbenzene, chloropropylbenzene, bromoethylbenzene, bromopropylbenzene, and phenoxybenztoluene. As a matter of course, the aromatic compounds are not limited to these examples.

The catalyst of the invention is very effective particularly to isomerization, disproportionation, and transalkylation. The reason for this is that in the isomerization, large substituent groups must move within the pore of the zeolite. In the disproportionation and transalkylation, it is thought that these reactions proceed through a state of two molecules linked as a reaction intermediate, and therefore the zeolite having a large pore size in particular is very effective. The conventional CFI-type catalysts have a small number of acid points and large crystals causing low diffusion within the pores, and fail to exercise sufficient performance in spite of pores as large as a fourteen-membered ring size.

The process for the conversion of the invention is effective to the isomerization of the aromatic compounds containing three or more substituent groups, for example, dihalogenated toluenes, trihalogenated benzenes, and trialkylbenzenes. More specifically, the process in particular is effective to the isomerization of dichlorotoluene, trichlorobenzene, and trimethylbenzene.

The process for the conversion also is not particularly limited, and both liquid phase and gas phase conversions are carried out. Reaction pressure and reaction temperature vary depending upon the kinds of conversion, and therefore are not limited. Although all fixed bed, moving bed, and fluidized bed processes can be used, a fixed-bed fluid system in particular is industrially preferred because of easy operations. The coexistence of hydrogen also is possible in order to reduce to coking.

EXAMPLES

The invention is illustrated through examples below.

Reference Example 1

Synthesis of Methylsparteinium Hydroxide

An aqueous solution of methylsparteinium hydroxide (hereinafter abbreviated as "ROH") was prepared as follows. 127 g of (−)-sparteine sulphate pentahydrate (Aldrich) was dissolved with stirring in 190 g of 10% aqueous NaOH solution, and extracted three times with 200 ml of toluene. The toluene layer combined was washed once with 200 ml of a saturated aqueous solution of NaCl, dried over potassium carbonate, and the toluene was evaporated with a rotary evaporator. The resulting dried product was recovered with 500 ml of acetone, and 127.7 g of methyl iodide was slowly added with stirring to precipitate white crystals. The crystals were washed with diethylether, and dried. The crystals were recrystallized from isopropanol, washed with a cold isopropanol and dried. The resulting product was identified as N(16)-methylsparteinium iodide by $^1$H-NMR and $^{13}$C-NMR measurements. The product was then dissolved in water, and was changed from the iodide to the hydroxide by use of anion-exchange resin IRA-410 (OH type). Thereafter, the hydroxide solution was concentrated with a rotary evaporator. The concentration of the resulting aqueous ROH solution was determined by titrating with aqueous hydrochloric acid by use of a phenolphthalein indicator. The concentration of the aqueous ROH solution was 2.219 m mol/g.

EXAMPLE 1

Synthesis of CIT-5

Ludox HS-30 (manufactured by du Pont Corp.) as a source of silica, aluminum nitrate nonahydrate (manufactured by Nakaraitesuku K.K.) as a source of aluminum, and anhydrous lithium hydroxide (manufactured by Kishida Kagaku K.K.) as a source of lithium were used to prepare a mixture having the following composition.

$SiO_2:0.1LiOH:0.4ROH:0.02Al(NO_3)_3:50H_2O$ (molar ratio)

Specifically, 0.055 g of anhydrous lithium hydroxide was dissolved in 5.71 g of distilled water, and 4.146 g of the aqueous ROH solution prepared in Reference Example 1 was then added and stirred for 10 min. Subsequently, a solution where 0.173 g of aluminum nitrate nonahydrate had been dissolved in 10 g of distilled water with stirring was added and stirred for 30 min. Furthermore, 4.609 g of Ludox HS-30 was added and stirred for 3 hr.

Figure 2:
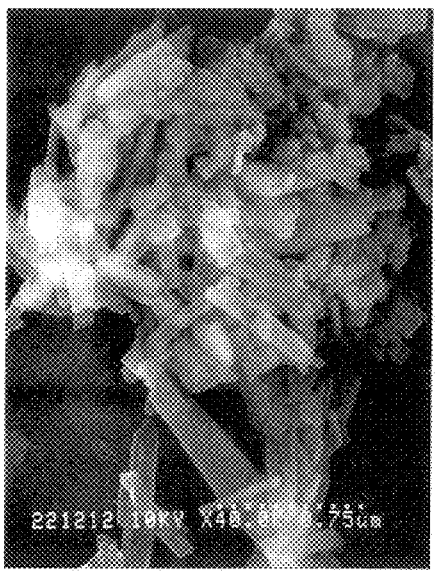
FIG. 2 is a field emission scanning electron micrograph (FE-SEM) of the CIT-5 synthesized in Example 1.

Part of the aforesaid mixture was placed in a 23-ml Teflon autoclave (manufactured by Pearl Co.). The autoclave was set in a rotary hydrothermal synthesis reactor (manufactured by Hiro K.K.), heated at 175° C. for 14 days while rotating at 60 rpm, and then cooled with water. Slurry in the autoclave was filtered, washed with water, and dried at 100° C. Measurement of X-ray diffraction gave a pattern as shown in FIG. 1, which showed the formation of CIT-5. Conditions of the X-ray diffraction are as follows; X-ray source: Cu/40kV/3 mA, Scanning speed: 3 degree/min. Measurement by a field emission scanning electron microscope (FE-SEM) indicated that crystals had shapes as shown in FIG. 2, and the long axes of almost all the crystals were 0.7 μm or less. Results of the elemental analysis of the crystals by X-ray fluorometry showed that the Si/Al ratio was 42.

EXAMPLE 2

Synthesis OF CIT-5

Ludox HS-30 (manufactured by du Pont Corp.) as a source of silica, H-type USY (Si/Al=25, PQ Corporation) as a source of aluminum, and anhydrous lithium hydroxide (manufactured by Kishida Kagaku K.K.) as a source of lithium were used, and a mixture having the following composition was prepared.

$SiO_2$:0.1LiOH:0.4ROH:0.01$Al_2O_3$:50$H_2O$ (molar ratio)

Specifically, 0.055 g of anhydrous lithium hydroxide was dissolved in 17.30 g of distilled water, and 4.146 g of the aqueous ROH solution prepared in Reference Example 1 was then added and stirred for 10 min. Subsequently, 0.806 g of USY was added with stirring and stirred for 30 min. Moreover, 2.303 g of Ludox HS-30 was added and stirred for 3 hr.

Figure 3:
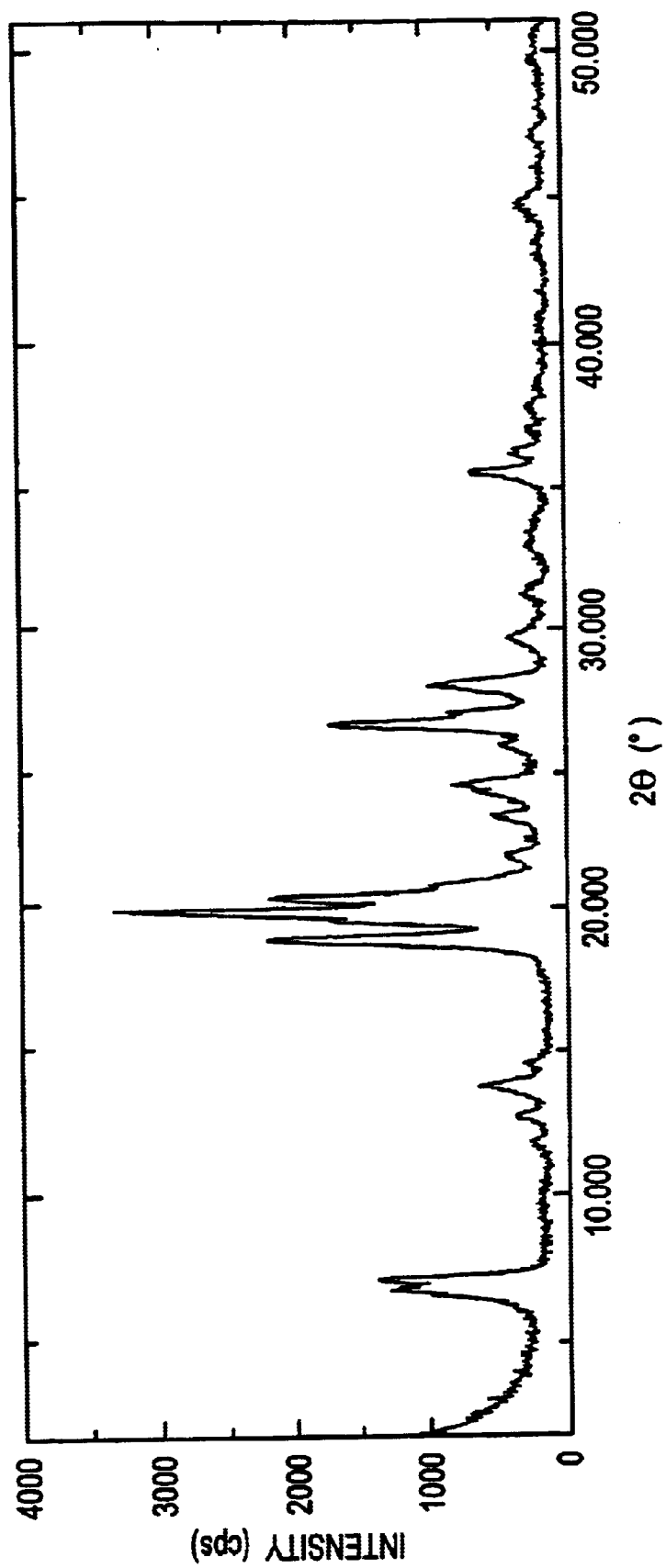
FIG. 3 is an X-ray diffraction pattern of CIT-5 synthesized in Example 2.

Part of the aforesaid mixture was placed in a 23-ml Teflon autoclave (manufactured by Pearl Co.). The autoclave was set in a rotary hydrothermal synthesis reactor (manufactured by Hiro K.K.), heated at 175° C. for eight days while rotating at 60 rpm, and then cooled with water. Slurry in the autoclave was filtered, washed with water, and dried at 100° C. Measurement of X-ray diffraction was carried out at conditions similar to Example 1 and gave a pattern as shown in FIG. 3, which showed the formation of CIT-5. Measurement of the shapes of crystals by a field emission scanning electron microscope showed that the long axes of the crystals were 0.7 μm or less. Results of the elementary analysis of the crystals by X-ray fluorometry revealed that the Si/Al ratio was 40.

EXAMPLE 3

Synthesis of CIT-5

H-type USY (Si/Al=54, manufactured by Tosoh Corp.) as a source of silica, aluminum nitrate nonahydrate (manufactured by Nakaraitesuku K.K.) as a source of aluminum, and anhydrous lithium hydroxide (manufactured by Kishida Kagaku K.K.) as a source of lithium were used, and a mixture having the following composition was prepared.

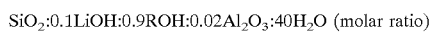

$SiO_2$:0.1LiOH:0.9ROH:0.02$Al_2O_3$:40$H_2O$ (molar ratio)

Specifically, 0.022 g of anhydrous lithium hydroxide was dissolved in 2.968 g of distilled water, and 3.650 g of the aqueous ROH solution prepared in Reference Example 1 was then added and stirred for 10 min. Subsequently, a solution prepared by dissolving 0.072 g of aluminum nitrate nonahydrate in 1.985 g of distilled water was added with stirring and stirred for 30 min. Moreover, 0.553 g of USY was added and stirred at 80° C. for 5 hr.

Figure 4:
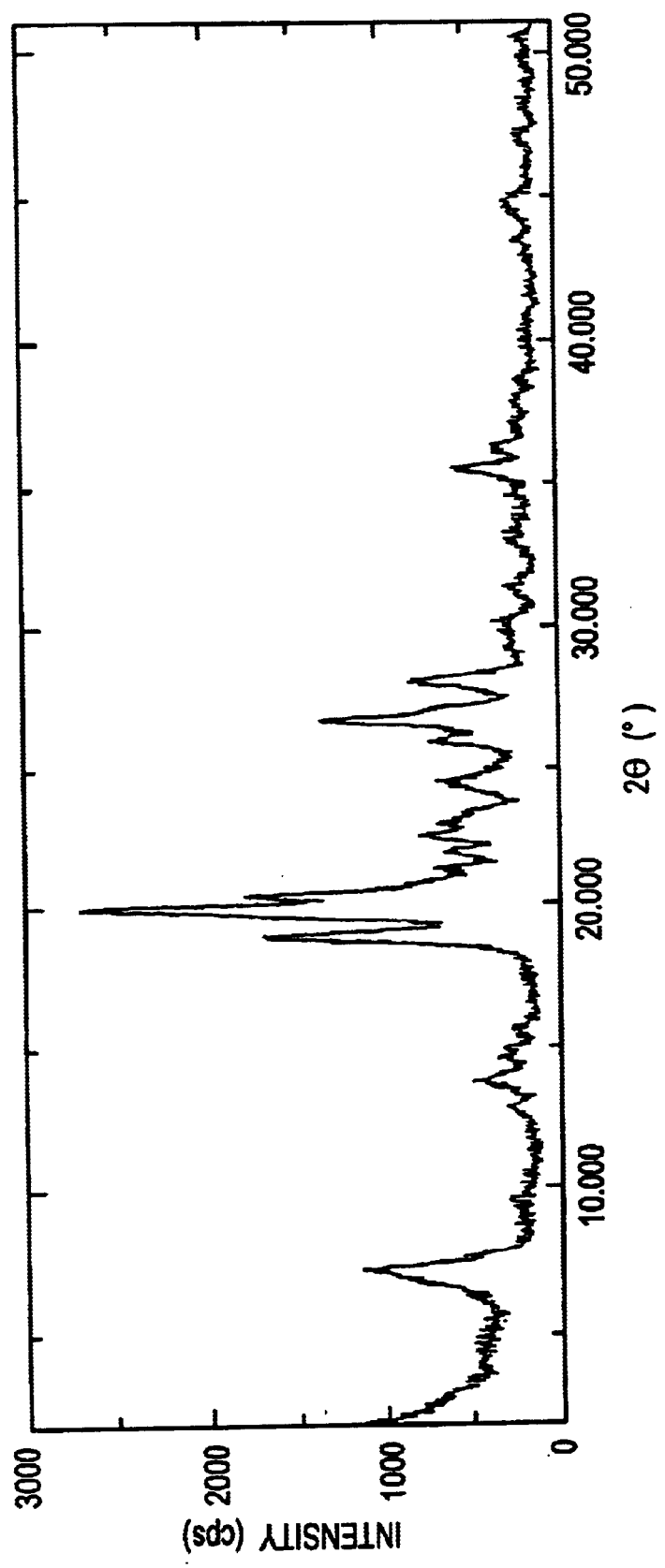
FIG. 4 is an X-ray diffraction pattern of CIT-5 synthesized in Example 3.

Part of the aforesaid mixture was placed in a 5-ml Teflon autoclave (manufactured by Flon Chemical K.K.). The autoclave was set in a rotary hydrothermal synthesis Reactor (manufactured by Hiro K.K.), heated at 182° C. for 14 days while rotating at 60 rpm, and then cooled with water. Slurry in the autoclave was filtered, washed with water, and dried at 100° C. Measurement of X-ray diffraction was carried out at conditions similar to Example 1, and gave a pattern as shown in FIG. 4, which showed the formation of CIT-5. Measurement by a field emission scanning electron microscope (FE-SEM) showed that the long axes of the crystals were 0.7 μm or less. Results of the elementary analysis by X-ray fluorometry revealed that the Si/Al ratio was 23.

EXAMPLE 4

Synthesis OF CIT-5

H-type USY (Si/Al=54, manufactured by Tosoh Corp.) as a source of silica, aluminum hydroxide (manufactured by Katayama Kagaku K.K.) as a source of aluminum, and anhydrous lithium hydroxide (manufactured by Kishida Kagaku K.K.) as a source of lithium were used, and a mixture having the following composition was prepared.

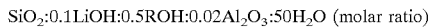

$SiO_2$:0.1LiOH:0.5ROH:0.02$Al_2O_3$:50$H_2O$ (molar ratio)

Specifically, 0.022 g of anhydrous lithium hydroxide was dissolved in 7.268 g of distilled water, and 2.028 g of the aqueous ROH solution prepared in Reference Example 1 was then added and stirred for 10 min. Subsequently, 0.015 g of aluminum hydroxide was added with stirring and stirred for 30 min. Moreover, 0.553 g of USY was added and stirred for 3 hr.

Figure 5:
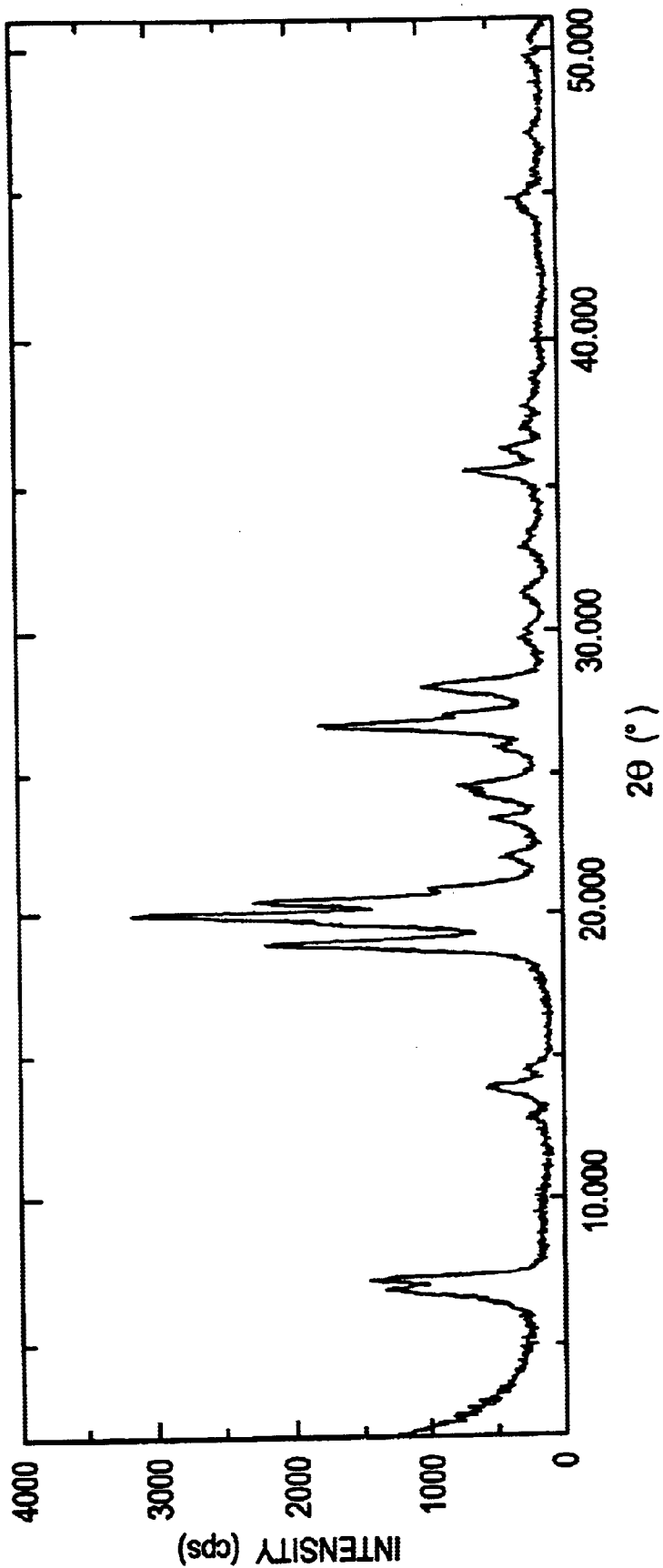
FIG. 5 is an X-ray diffraction pattern of CIT-5 synthesized in Example 4.

Part of the aforesaid mixture was placed in a 5-ml Teflon autoclave (manufactured by Flon Chemical K.K.). The autoclave was set in a rotary hydrothermal synthesis reactor (manufactured by Hiro K.K.), heated at 182° C. for seven days while rotating at 60 rpm, and cooled with water. Slurry in the autoclave was filtered, washed with water, and dried at 100° C. Measurement of X-ray diffraction at conditions similar to Example 1 gave a pattern as shown in FIG. 5, which showed the formation of CIT-5. Measurement by a field emission scanning electron microscope (FE-SEM) showed that the long axes of crystals were 0.7 μm or less. Results of the elementary analysis of the crystals revealed that the Si/Al ratio was 26.

EXAMPLE 5

Synthesis of CIT-5

H-type HSY (Si/Al=54, manufactured by Tosoh Corp.) as a source of silica, aluminum hydroxide (manufactured by Katayama Kagaku K.K.) as a source of aluminum, and anhydrous lithium hydroxide (manufactured by Kishida Kagaku K.K.) as a source of lithium were used, and a mixture having the following composition was prepared.

$SiO_2$:0.12LiOH:0.3ROH:0.02$Al_2O_3$:50$H_2O$ (molar ratio)

Specifically, 0.026 g of anhydrous lithium hydroxide was dissolved in 7.599 g of distilled water, and 1.217 g of the aqueous ROH solution prepared in Reference Example 1 was then added and stirred for 10 min. Subsequently, 0.015 g of aluminum hydroxide was added with stirring and stirred for 30 min. Moreover, 0.553 g of USY was added and stirred for 3 hr.

Figure 6:
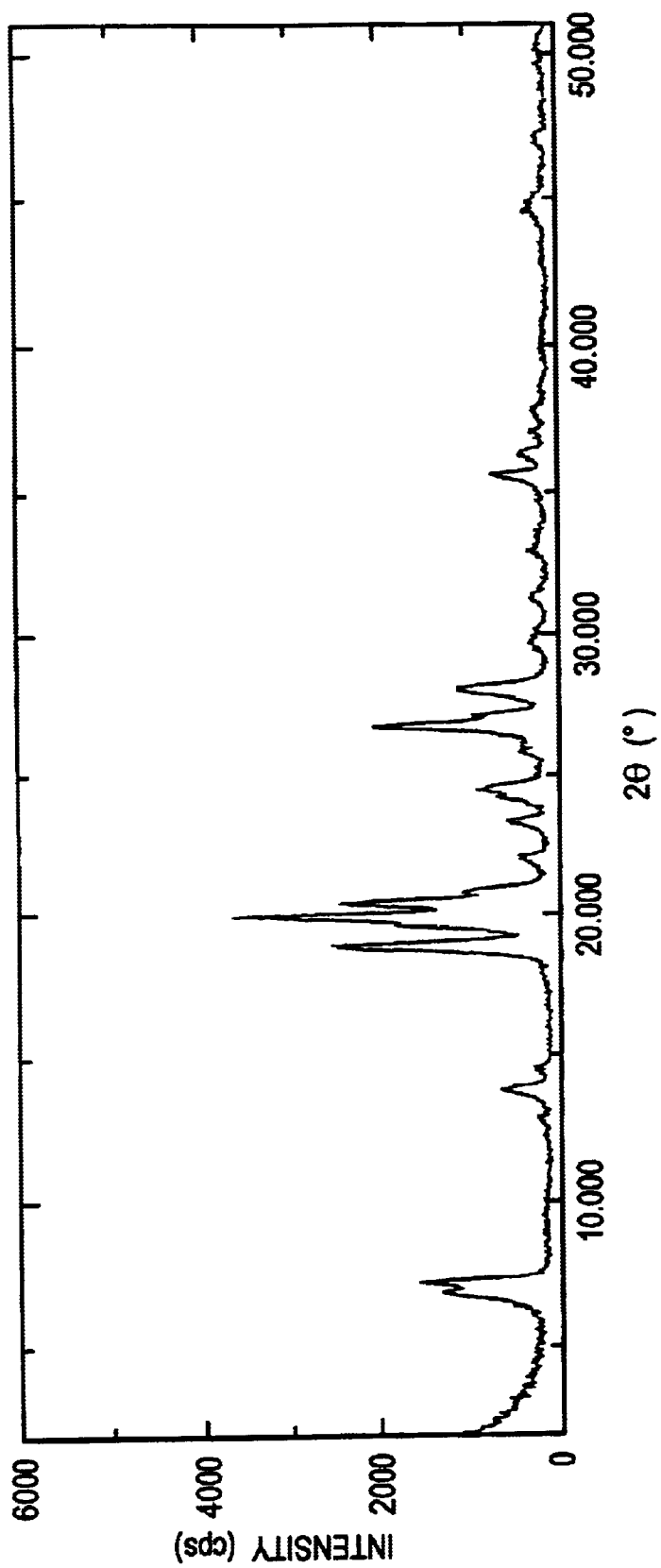
FIG. 6 is an X-ray diffraction pattern of CIT-5 synthesized in Example 5.

Part of the aforesaid mixture was placed in a 5-ml Teflon autoclave (manufactured by Flon Chemical K.K.). The autoclave was set in a rotary hydrothermal synthesis reactor (manufactured by Hiro K.K.), heated at 182° C. for 10 days while rotating at 60 rpm), and then cooled with water. Slurry in the autoclave was filtered, washed with water, and dried at 100° C. Measurement of X-ray diffraction was carried out at conditions similar to Example 1, and gave a pattern as shown in FIG. 6, which showed the formation of CIT-5. Measurement by a field emission scanning electron microscope (FE-SEN) showed that the long axes of crystals were 0.7 μm or less. Results of the elementary analysis of the crystals revealed that the Si/Al ratio was 24.

EXAMPLE 6

Synthesis of CIT-5

H-type USY (Si/Al=54, manufactured by Tosoh Corp.) as a source of silica, aluminum hydroxide (manufactured by Katayama Kagaku K.K.) as a source of aluminum, and anhydrous lithium hydroxide (manufactured by Kishida Kagaku K.K.) as a source of lithium were used, and a mixture having the following composition was prepared.

$SiO_2:0.12LiOH:0.5ROH:0.033Al_2O_3:50H_2O$ (molar ratio)

Specifically, 0.026 g of anhydrous lithium hydroxide was dissolved in 7.268 g of distilled water, and 2.028 g of the aqueous ROH solution prepared in Reference Example 1 was then added and stirred for 10 min. Subsequently, 0.034 g of aluminum hydroxide was added with stirring and stirred for 30 min. Moreover, 0.553 g of USY was added and stirred for 3 hr.

Figure 7:
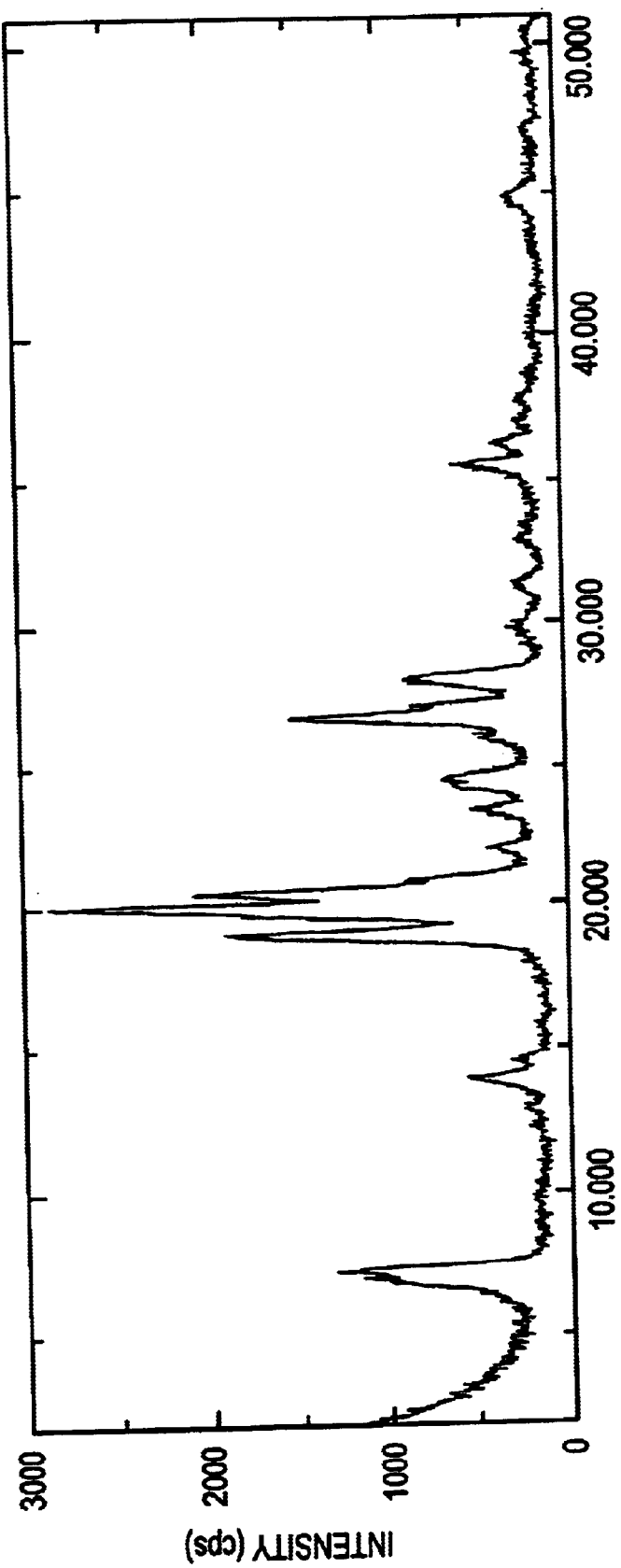
FIG. 7 is an X-ray diffraction pattern of CIT-5 synthesized in Example 6.

Part of the aforesaid mixture was placed in a 5-ml Teflon autoclave (manufactured by Flon Chemical K.K.). The autoclave was set in a rotary hydrothermal synthesis reactor (manufactured by Hiro K.K.), heated at 182° C. for 8 days while rotating at 60 rpm, and then cooled with water. Slurry in the autoclave was filtered, washed with water, and dried at 100° C. Measurement of X-ray diffraction was carried out at conditions similar to Example 1, and gave a pattern as shown in FIG. 7, which showed the formation of CIT-5. Measurement by a field emission scanning electron microscope (FE-SEM) showed that the long axes of crystals were 0.7 μm or less. Results of the elementary analysis of the crystals by X-ray fluorometry revealed that the Si/Al ratio was 20.

Comparative Example 1

Synthesis of Known CIT-5

Ludox HS-30 (manufactured by du Pont Corp.) as a source of silica, aluminum nitrate nonahydrate (manufactured by Nakaraitesuku K.K.) as a source of aluminum, and anhydrous lithium hydroxide (manufactured by Kishida Kagaku K.K.) as a source of lithium were used, and a mixture having the following composition was prepared.

$SiO_2:0.1LiOH:0.2ROH:0.01Al(NO_3)_3:50H_2O$ (molar ratio)

Specifically, 0.055 g of anhydrous lithium hydroxide was dissolved in 5.71 g of distilled water, and 2.073 g of the aqueous ROH solution prepared in Reference Example 1 was added and stirred for 10 min. Subsequently, a solution prepared by dissolving 0.087 g of aluminum nitrate nonahydrate in 10 g of distilled water was added with stirring and stirred for 30 min. Moreover, 4.609 g of Ludox HS-30 was added and stirred for 3 hr.

Figure 9:
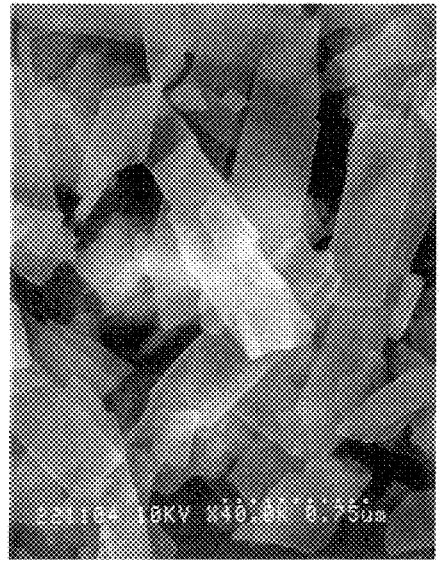
FIG. 9 is a field emission scanning electron micrograph (FE-SEM) of CIT-5 synthesized in Comparative Example 1.
Figure 8:
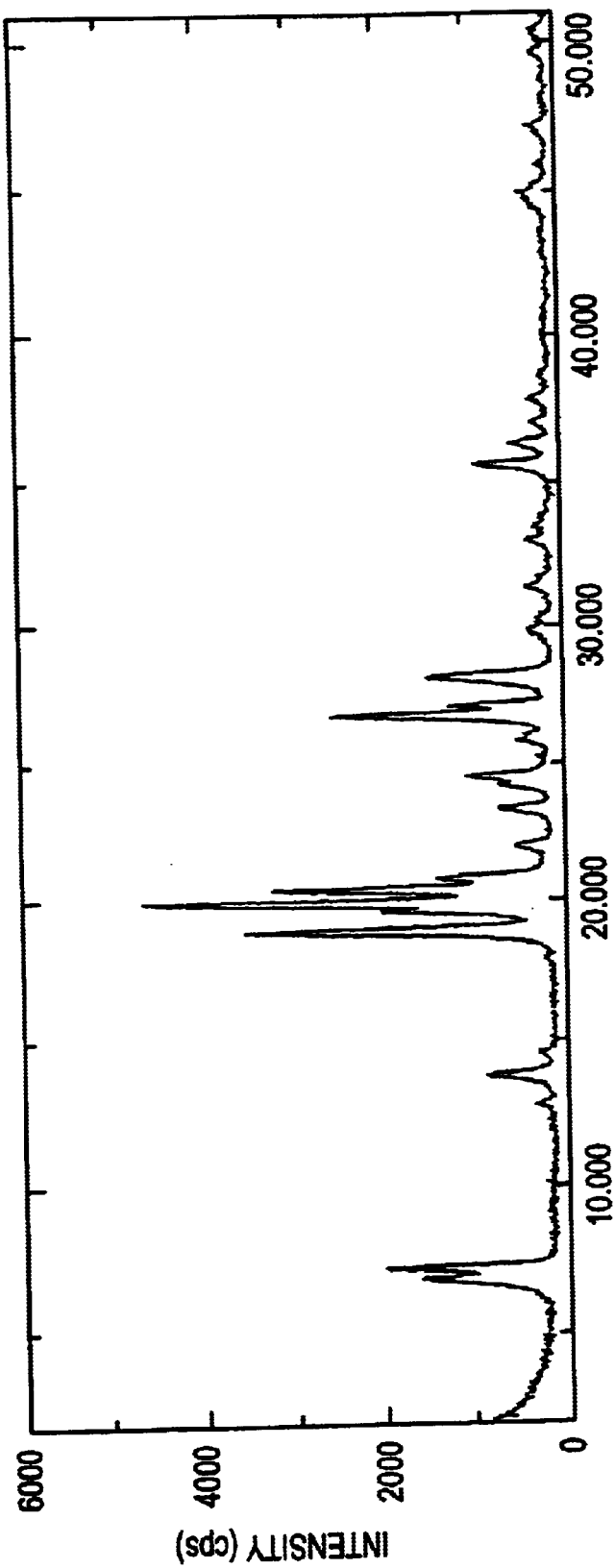
FIG. 8 is an X-ray diffraction pattern of CIT-5 synthesized in Comparative Example 1.

Part of the aforesaid mixture was placed in a 23-ml Teflon autoclave (manufactured by Pearl Co.). The autoclave was set in a rotary hydrothermal synthesis reactor (manufactured by Hiro K.K.), heated at 175° C. for 14 days while rotating at 60 rpm, and then cooled with water. Slurry in the autoclave was filtered, washed with water, and dried at 100° C. Measurement of X-ray diffraction gave a pattern as shown in FIG. 8, which ensured the formation of CIT-5. Measurement by a field emission scanning electron microscope (FE-SEM) showed that crystals had shapes as shown in FIG. 9, and the long axes of the crystals were greater than 0.7 μm. Results of the elementary analysis of the crystals by X-ray fluorometry revealed that the Si/Al ratio was 95.

Comparative Example 2

(Supplementary Examination of Literature 2; *Chemical Communications*, 2179 (1997))

Ludox HS-30 (manufactured by du Pont Corp.) as a source of silica, aluminum nitrate nonahydrate (manufactured by Nakaraidesuku K.K.) as a source of aluminum, and anhydrous lithium hydroxide (manufactured by Katayama Kagaku K.K.) as a source of lithium were used, and a mixture having the following composition was prepared.

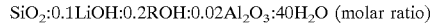

$SiO_2:0.1LiOH:0.2ROH:0.02Al_2O_3:40H_2O$ (molar ratio)

Specifically, 0.055 g of anhydrous lithium hydroxide was dissolved in 2.880 g of distilled water, and 2.073 g of the aqueous ROH solution prepared in Reference Example 1 was then added and stirred for 10 min. Subsequently, a solution prepared by dissolving 0.345 g of aluminum nitrate nonahydrate in 9.459 g of distilled water was added with stirring and stirred for 30 min. Moreover, 4.609 g of Ludox HS-30 was added and stirred for 3 hr.

Figure 10:
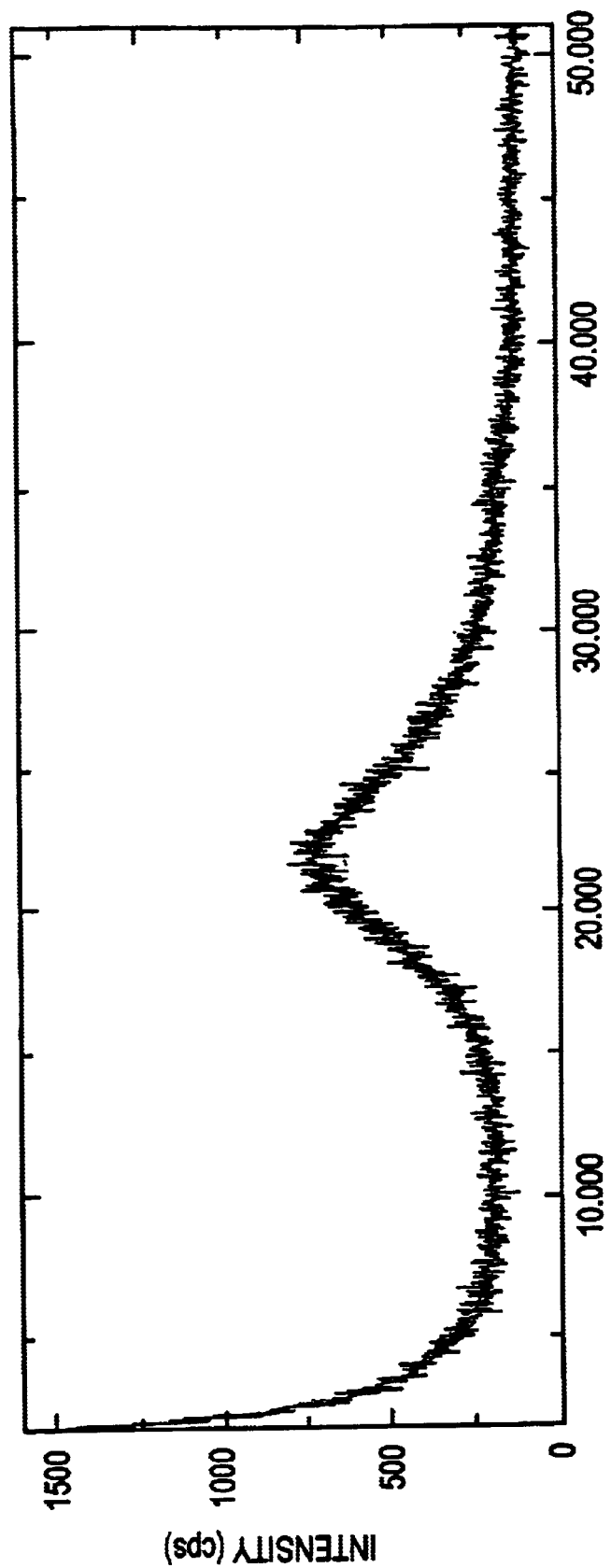
FIG. 10 is an X-ray diffraction pattern of CIT-5 synthesized in Comparative Example 2.

Part of the aforesaid mixture was placed in a 23-ml Teflon autoclave (manufactured by Pearl Co.). The autoclave was set in a rotary hydrothermal synthesis reactor (manufactured by Hiro K.K.), heated at 175° C. for 12 days while rotating at 60 rpm, and then cooled with water. Slurry in the autoclave was filtered, washed with water, and dried at 100° C. Measurement of X-ray diffraction gave a pattern as shown in FIG. 10. The product was an amorphous substance. The process described in literature 2 failed to form CIT-5.

EXAMPLE 7

Preparation of Catalyst

Figure 11:
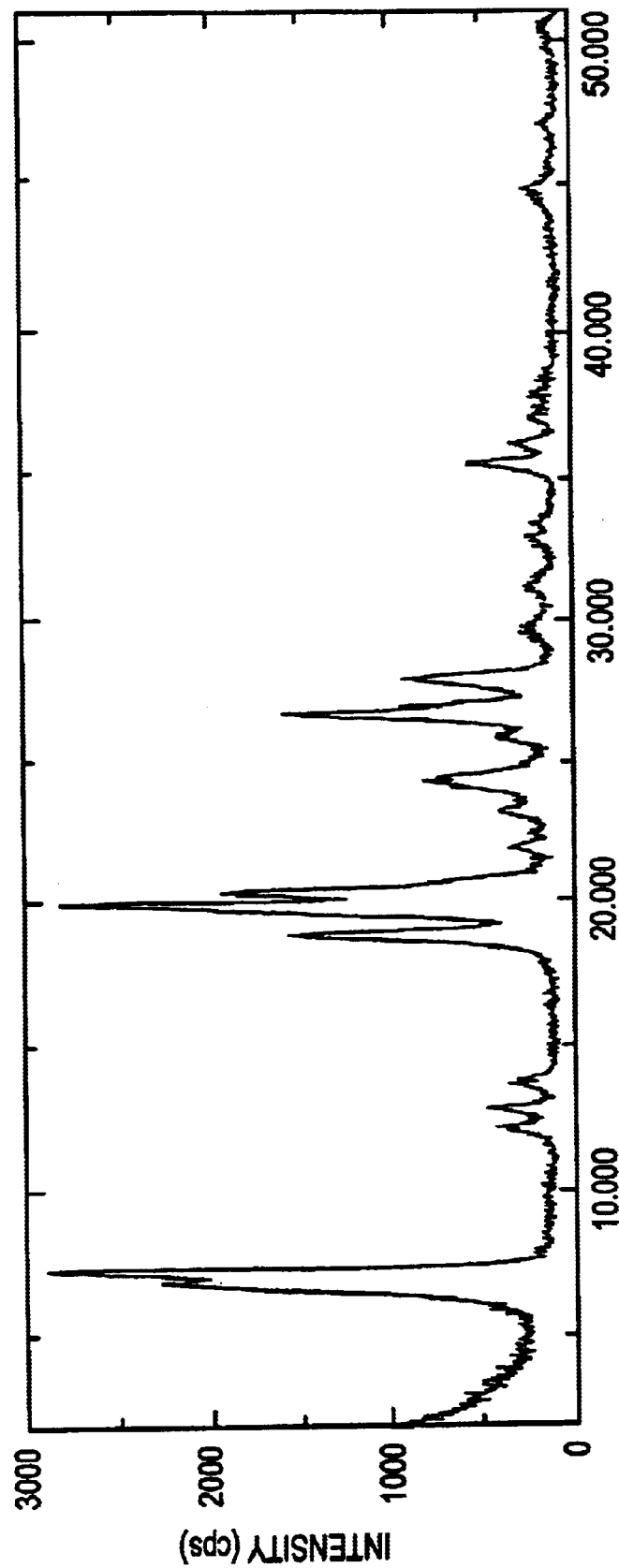
FIG. 11 is an X-ray diffraction pattern of CIT-5 calcined in Example 7.

CIT-5 powder prepared in Example 1 was calcined at 600° C. for 3 hr and then cooled. An X-ray diffraction pattern of the powder calcined is shown in FIG. 11. 30 g of a 10 weight percent aqueous solution of ammonium chloride was added to 0.6 g of the powder and heated at 80° C. for 1 hr. Liquid was separated by decantation, and the residual was washed with 30 g of water. This operation was repeated four times, and the last residual was sufficiently washed with 80° C. water. This was dried at 120° C. for one day and underwent tablet pressing. The product was pulverized, meshed to 12–60, and calcined at 540° C. for 3 hr to prepare a catalyst.

Comparative Example 3

Preparation of Comparative Catalyst

CIT-5 powder of Comparative Example 1 was calcined at 600° C. for 3 hr, cooled, and pulverized. 30 g of a 10 weight percent aqueous solution of ammonium chloride was added to 0.6 g of the pulverized product, and heated at 80° C. for 1 hr. Liquid was separated by decantation, and the residual was washed with 30 g of water. This operation was repeated four times, and the last residual was sufficiently washed with 80° C. water. This was dried at 120° C. for one day and underwent tablet pressing. The pressed product was pulverized, meshed to 12–60, and calcined at 540° C. for 3 hr to prepare a catalyst.

EXAMPLE 8

Conversion Reaction

The catalyst of Example 7 calcined at 540° C. for 3 hr was cooled in a desiccator containing diphosphorus pentaoxide. 2.0 g of 2,4-dichlorotoluene (2,4-DCT) was placed in a 5-ml stainless autoclave, and 0.5 g of the catalyst cooled in the desiccator was then added and sealed. This was kept in an oven maintained at 350° C. for 3 hr. After cooling the product was analyzed by gas chromatography. The catalyst of Comparative Example 3 also was subjected to a similar reaction.

Results of the Conversion Reaction of 2,4-DCT

The degree of conversion of 2,4-DCT was 40 percent in use of the catalyst of Example 7, and 10 percent in use of the catalyst of Comparative Example 3. The activity of the catalyst was heightened, exceeding that expected from the Si/Al ratio of CIT-5. This result reveals that the CIT-5 zeolite in the present catalyst has not only a lower Si/Al ratio, but also smaller crystals than conventional CIT-5's.

What is claimed is:

1. A CFI-type zeolite comprising an atomic ratio of silicon to a heteroatom of 45 or less, and long axes of crystals of 0.7 μm or less.

2. The CFI-type zeolite as described in claim 1 wherein the heteroatom is at least one atom selected from aluminum, gallium, iron, titanium, boron, cobalt, and chromium.

3. A catalyst comprising the zeolite as described in claim 1.

4. The catalyst as described in claim 3 wherein the zeolite is of an acid type.

5. The catalyst as described in claim 3 further comprising rhenium.

6. A catalyst for conversion reaction of aromatic compounds having three or more substituent groups on an aromatic ring, wherein said catalyst comprises the zeolite as described in claim 1.

7. A catalyst for isomerization reaction of aromatic compounds having three or more substituent groups on an aromatic ring, wherein said catalyst comprises the zeolite as described in claim 1.

8. The catalyst as described in claim 6 or 7 wherein the aromatic compounds are dihalogenated toluenes, trihalogenated benzenes, and trialkylbenzenes.

9. A process for preparing CFI-type zeolite comprising the steps of:
   preparing a reaction mixture having
      (1) a molar ratio of $LiOH/SiO_2 < 0.15$; and
      (2) a molar ratio of $ROH/SiO_2 > 0.3$ (molar ratio, ROH is an alkylsparteinium hydroxide); and
   subjecting said reaction mixture to hydrothermal treatment to produce a CFI-type zeolite having an atomic ratio of silicon to a heteroatomic ratio of silicon to a heteroatom of 45 or less, and long axes of crystals are 0.7 μm or less.

* * * * *

UNITED STATES PATENT AND TRADEMARK OFFICE
CERTIFICATE OF CORRECTION

PATENT NO.   : 6,635,233 B2
DATED        : October 21, 2003
INVENTOR(S)  : Kato et al.

It is certified that error appears in the above-identified patent and that said Letters Patent is hereby corrected as shown below:

Column 5,
Line 3, please change the following compound from:

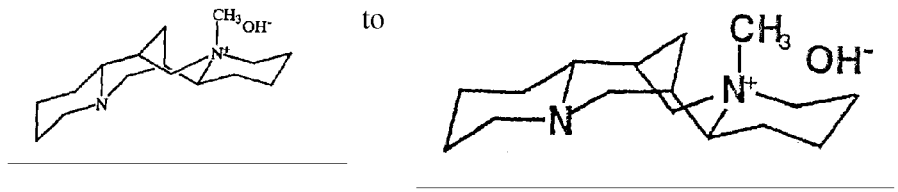

Signed and Sealed this

Twentieth Day of April, 2004

JON W. DUDAS
*Acting Director of the United States Patent and Trademark Office*